United States Patent
Krebs et al.

(10) Patent No.: US 10,045,787 B2
(45) Date of Patent: Aug. 14, 2018

(54) ORTHOPEDIC DEVICE HOLDER SYSTEM (71) Applicant: Zimmer, Inc., Warsaw, IN (US)

(72) Inventors: Robert D. Krebs, Warsaw, IN (US); Lisa Carlin, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 316 days.

(21) Appl. No.: 14/878,358

(22) Filed: Oct. 8, 2015

(65) Prior Publication Data
US 2016/0100872 A1 Apr. 14, 2016

Related U.S. Application Data (60) Provisional application No. 62/063,042, filed on Oct. 13, 2014.

(51) Int. Cl.
*A61B 17/16* (2006.01)
*A61B 17/00* (2006.01)
*A61B 17/88* (2006.01)

(52) U.S. Cl.
CPC ........ *A61B 17/162* (2013.01); *A61B 17/8872* (2013.01); *A61B 17/8875* (2013.01); *A61B 2017/00464* (2013.01)

(58) Field of Classification Search
CPC .............. A61B 17/162; A61B 17/1633; A61B 17/1617
See application file for complete search history.

(56) References Cited

U.S. PATENT DOCUMENTS 5,766,190 A * 6/1998 Wulfman ........... A61B 17/1617
606/159
7,766,585 B2 * 8/2010 Vasudeva .............. B23B 31/005
279/22

* cited by examiner

*Primary Examiner* — Andrew Yang
(74) *Attorney, Agent, or Firm* — Schwegman Lundberg & Woessner, P.A.

(57) ABSTRACT

Orthopedic device holder systems including a quick connect between an orthopedic device holder and an orthopedic tool are disclosed. The orthopedic device holder can include a shaft having a shaft connection end including at least three shaft engaging surfaces. The orthopedic tool can have a tool connection end including at least three tool engaging surfaces configured to couple with the three shaft engaging surfaces of the orthopedic device holder.

19 Claims, 5 Drawing Sheets

FIG. 11C

ORTHOPEDIC DEVICE HOLDER SYSTEM

CLAIM OF PRIORITY

This application claims the benefit of U.S. Provisional Patent Application Ser. No. 62/063,042 filed on Oct. 13, 2014, the benefit of priority of which is claimed hereby, and which is incorporated by reference herein in its entirety.

TECHNICAL FIELD

This patent document pertains generally, but not by way of limitation, to an orthopedic device holder system, including a quick connect between an orthopedic device holder and an orthopedic tool.

BACKGROUND

Tools or other instruments can be used by a surgeon to complete a surgical procedure (e.g., an orthopedic procedure). For example, intramedullary rods, drill guides, reamers, and pin and screw drivers can be used during the orthopedic procedure. During the procedure, when different instruments or devices are being used, the surgeon may have to switch between various device holders, which can increase surgery time.

OVERVIEW

The present inventors recognize, among other things, that an orthopedic device holder system having a quick connect and release configuration between an orthopedic device holder and an orthopedic tool can be beneficial. The orthopedic device holder system of the present disclosure can provide a quick connect between the orthopedic device holder and the orthopedic tool while providing a firm connection that allows for secure forward and reverse rotation and can minimize sideways movement. Additionally, the orthopedic device holder can quickly connect and release the orthopedic tool such that the orthopedic device holder can be readily used with different orthopedic tools.

Previous quick connect devices can include a collet connection and a chuck connection. The collet connection generally has a piece that must be forced over or through a device to expand a ringed area and engage a groove in an opposite piece. The chuck connection generally includes an outer component having a plurality of teeth, wherein turning the outer component moves the teeth inward to tighten the outer component on an inner component inserted within the outer component. Other quick connect devices can include a collar that can be pushed forward by a spring to force a plurality of ball bearings into locking engagement with a groove on an opposite piece. Orthopedic device holder systems of the present disclosure can eliminate the threading involved in the collet or chuck connection. Furthermore, orthopedic device holder systems of the present disclose can offer the speed of the ball bearing quick connect devices without the inherent danger of the ball bearings separating from the device, as well as cleaning issues that are present with such devices having numerous moving pieces. Additionally, the low-profile design of the orthopedic device holder systems of the present disclosure allow for use on modular devices that require maximum rigidity on a small diameter shaft.

To further illustrate the orthopedic device holder system disclosed herein, a non-limiting list of examples is provided here:

In Example 1, a system comprises an orthopedic device holder, including a shaft having a proximal end and a distal end, the shaft including a shaft connection end positioned at the distal end of the shaft, the shaft connection end having at least three shaft engaging surfaces, and an orthopedic tool having a proximal end and a distal end, the orthopedic tool configured to be coupled to the orthopedic device holder. The orthopedic tool can include a tool connection end positioned at the proximal end of the orthopedic tool configured to engage with the shaft connection end, the tool connection end having at least three tool engaging surfaces, and an orthopedic tool portion, where a first shaft engaging surface is configured to mate with a first tool engaging surface, a second shaft engaging surface is configured to mate with a second tool engaging surface, and a third shaft engaging surface is configured to mate with a third tool engaging surface.

In Example 2, Example 1 is optionally configured such that the first shaft engaging surface and the first tool engaging surface have opposite mating surfaces, the second shaft engaging surface and the second tool engaging surface have opposite mating surfaces, and the third shaft engaging surface and the third tool engaging surface have a similar mating surface.

In Example 3, Examples 1 or 2 are optionally configured such that the first and second shaft engaging surfaces and the first and second tool engaging surfaces have non-flat surfaces and the third shaft engaging surface and the third tool engaging surface have a flat surface.

In Example 4, Examples 1 through 3 are optionally configured such that the first shaft engaging surface and the second tool engaging surface have a concave shape and the second shaft engaging surface and the first tool engaging surface have a convex shape.

In Example 5, Examples 1 through 4 are optionally configured such that the shaft includes a collar portion and an elongate portion extending from the collar portion.

In Example 6, Example 5 is optionally configured such that the elongate portion extends between the collar portion and the shaft connection end.

In Example 7, Example 5 is optionally configured to include a resilient member positioned around the elongate portion adjacent to the collar portion, and a sleeve positioned around the shaft and adjacent to the resilient member.

In Example 8, Example 7 is optionally configured such that the sleeve defines a bore that receives the elongate portion of the shaft.

In Example 9, Example 7 is optionally configured such that the sleeve is moveable between a first position and a second position, such that in the first position the resilient member is in a compressed state and the shaft connection end extends from the sleeve and in the second position, the resilient member is in an less compressed state as compared to the compressed state such that the shaft connection end and the tool engaging end are positioned within the sleeve.

In Example 10, Example 9 is optionally configured such that at the second position, a distal end of the sleeve abuts the orthopedic tool portion.

In Example 11, Example 7 is optionally configured such that the elongate portion includes a locking projection.

In Example 12, Example 11 is optionally configured such that the sleeve defines a locking slot that is configured to receive the locking projection, the sleeve moveable between an unlocked position and a locked position, such that in the unlocked position, the sleeve is movable relative to the elongate portion and in the locked position, the sleeve is fixed relative to the elongate portion.

In Example 13, Examples 1 through 12 are optionally configured such that the proximal end of the shaft includes an engagement end configured to receive a turning device.

In Example 14, Examples 1 through 13 are optionally configured such that the shaft defines a longitudinal axis and the three shaft engaging surfaces are perpendicular to the longitudinal axis.

In Example 15, a system includes an orthopedic device holder, including a shaft having a shaft connection end having at least a first shaft engaging surface, a second shaft engaging surface, and a third shaft engaging surface, a resilient member positioned around the shaft, and a sleeve positioned around the shaft and adjacent to the resilient member, and an orthopedic tool having a tool connection end configured to engage with the shaft connection end, the tool connection end having a first tool engaging surface, a second tool engaging surface, and a third tool engaging surface, where the first shaft engaging surface is configured to mate with the first tool engaging surface, the second shaft engaging surface is configured to mate with the second tool engaging surface, and the third shaft engaging surface is configured to mate with the third tool engaging surface, and where the sleeve is configured to move between a first position and a second position such that at the first position, the shaft connection end extends from the sleeve and at the second position, the shaft connection end and the tool connection end are positionable within the sleeve.

In Example 16, Example 15 is optionally configured such that the first shaft engaging surface and the first tool engaging surface have opposite mating surfaces, and wherein the second shaft engaging surface and the second tool engaging surface have opposite mating surfaces.

In Example 17, Examples 15 or 16 are optionally configured such that the third shaft engaging surface and the third tool engaging surface have flat surfaces.

In Example 18, Examples 15 through 17 are optionally configured such that the third shaft engaging surface and the third tool engaging surface have opposite mating surfaces.

In Example 19, a method includes forming an orthopedic device holder having a shaft including a collar, an elongated portion extending from the collar, and a shaft connection end, the shaft connection end including at least a first shaft engaging surface, a second shaft engaging surface, and a third shaft engaging surface, and forming an orthopedic tool having a tool connection end configured to engage with the shaft connection end and a tool portion, the tool connection end having at least a first tool engaging surface, a second tool engaging surface, and a third tool engaging surface, wherein the first shaft engaging surface and the first tool engaging surface have opposite mating surfaces, and the second shaft engaging surface and the second tool engaging surface have opposite mating surfaces.

In Example 20, Example 19 is optionally configured to include positioning a resilient member around the shaft, and positioning a sleeve around the shaft and adjacent to the resilient member.

In Example 21, the orthopedic device holder systems or methods of any one or any combination of Examples 1-20 can optionally be configured such that all elements or options recited are available to use or select from.

These and other examples and features of the present orthopedic device holder systems and methods will be set forth in part in the following Detailed Description. This Overview is intended to provide non-limiting examples of the present subject matter—it is not intended to provide an exclusive or exhaustive explanation. The Detailed Description below is included to provide further information about the present orthopedic device holder system and method.

BRIEF DESCRIPTION OF THE DRAWINGS

In the drawings, like numerals can be used to describe similar elements throughout the several views. Like numerals can be used to represent different views or configurations of similar elements. The drawings illustrate generally, by way of example, but not by way of limitation, various embodiments discussed in the present document.

DETAILED DESCRIPTION

The present orthopedic device holder system is configured to provide a quick and easy releasable connection for a plurality of orthopedic tools (e.g., devices, instruments, etc.) with an orthopedic device holder. The orthopedic device holder system can include a quick connect such that the operator can readily switch between various orthopedic tools while providing a secure connection. For example, the orthopedic device holder system of the present disclosure can provide a quick connect device, allowing for forward and reverse rotation, and controlled insertion and extraction. Further, the quick connection between the orthopedic device holder and the orthopedic tool aids in easy assembly and can minimize sideways movement during use. The orthopedic device holder, the orthopedic tool, and their components can be made of a wide variety of materials, such as metal alloys, stainless steels, aluminum, titanium, polymers, carbon fiber, or combinations thereof.

Figure 1:
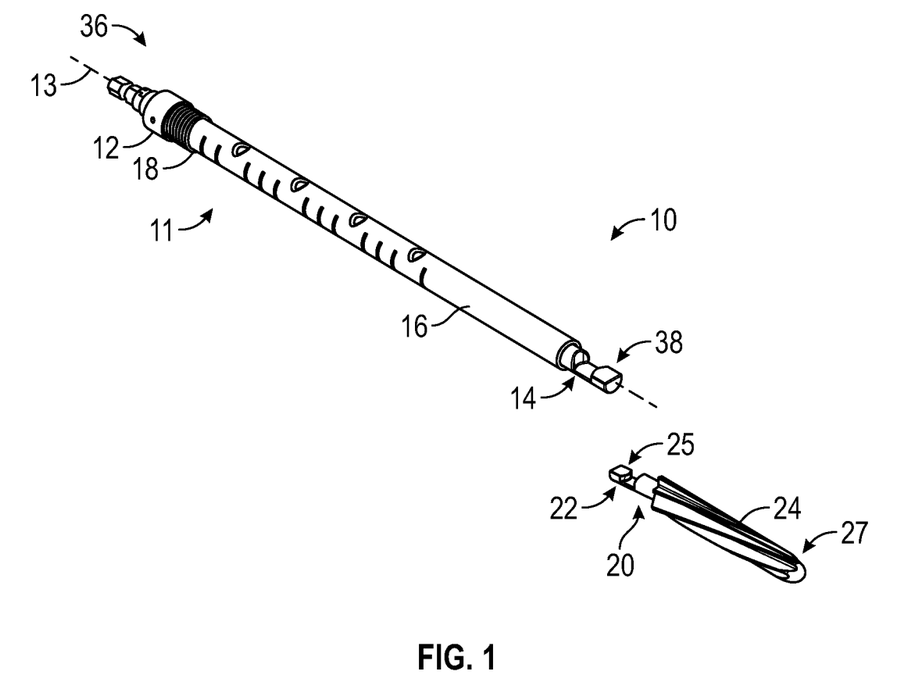
FIG. 1 illustrates a perspective view of an orthopedic device holder system including an orthopedic device holder and an orthopedic tool, in accordance with at least one example.

FIG. 1 illustrates a perspective view of an orthopedic device holder system 10 including an orthopedic device holder 11 and an orthopedic tool 20, as constructed in accordance with at least one example. The orthopedic device holder 11 (also referred to herein as "device holder 11") can include a shaft 12, a resilient member 18, and a sleeve 16. The resilient member 18 and the sleeve 16 can be positioned around a portion of the shaft 12. The shaft 12 can include a proximal end 36 and a distal end 38. As illustrated in FIG. 1, a shaft connection end 14 can be positioned at the distal end 38 of the shaft 12. The shaft connection end 14, as discussed herein, can be configured to engage with the orthopedic tool 20 (also referred to herein as "tool 20"). The orthopedic tool 20 can include a proximal end 25 and a distal end 27. The orthopedic tool 20 can include a tool connection end 22 positioned at the proximal end 25. The tool connection end 22 can be configured to engage with the shaft connection end 14 of the device holder 11. The distal end 27 of the tool 20 can include an orthopedic tool portion 24, e.g., a reamer, as shown in FIG. 1. However, other orthopedic tools, as discussed herein, can be utilized such as, but not limited to, a bit, a drill, and a driver (as shown in FIGS. 15A-15D).

The sleeve 16 can be moveable about the shaft 12. For example, the sleeve 16 can rotate about and move along a longitudinal axis 13 of the shaft 12. In an example, the sleeve 16 can be pulled back (in a direction toward the proximal end 36 of the shaft 16) to expose the shaft connection end 14. That is, the shaft connection end 14 extends from the sleeve 16, when the sleeve 16 is retracted. Once exposed, the shaft connection end 14 can be connected to the tool connection end 22. When the sleeve 16 is pulled back to expose the shaft connection end 14, the resilient member 18 can be in a compressed stated.

Figure 2:
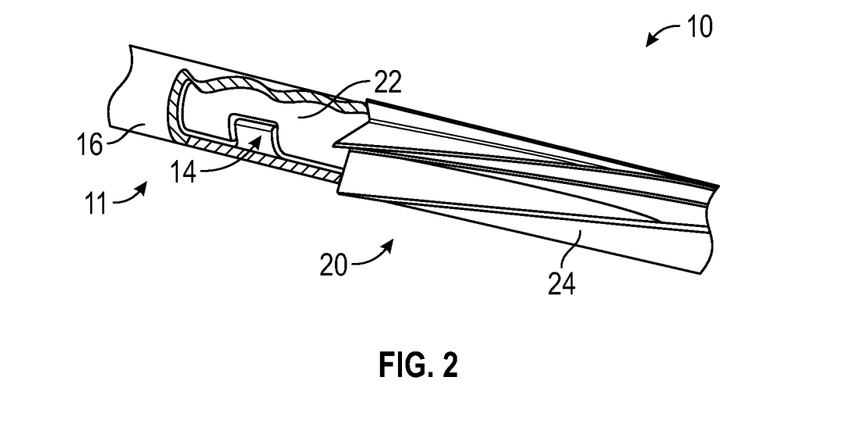
FIG. 2 illustrates a perspective view of a portion of the orthopedic tool holder system in FIG. 1 as assembled, in accordance with at least one example.

To secure the connection between the device holder 11 and the tool 20, the sleeve 16 can be released such that the sleeve 16 advances forward (in a direction toward the distal end 38 of the shaft 16). The resilient member 18 can transition from the compressed state to an uncompressed state or a less compressed state and the sleeve 16 can advance forward and extend to at least the end of the shaft connection end 14. In an example, the sleeve 16 can extend beyond the shaft connection end 14. For example, the sleeve 16 can advance forward until the sleeve 16 encircles both the shaft connection end 14 and the tool connection end 22, as shown in FIG. 2. The sleeve 16 can advance forward until the sleeve 16 abuts a portion of the tool 20. In an example, when the sleeve 16 abuts a portion of the tool 20, the resilient member 18 can be in a partially compressed state, such that the resilient member 18 applies a force to the sleeve 16 in the direction toward the distal end 38 of the shaft 12.

FIG. 2 illustrates a perspective view of a portion of the orthopedic tool holder system 10 in FIG. 1 as assembled, in accordance with at least one example. As seen in FIG. 2, a portion of the sleeve 16 is cut away to show the shaft connection end 14 and the tool connection end 22 engaged with each other within the sleeve 16. Since the sleeve encircles both the shaft connection end 14 and the tool connection end 22, the sleeve 16 can reduce the risk of the device holder 11 and the tool 20 separating during use. Further, because of the unique shape of the shaft connection end 14 and the tool connection end 22, sideways movement between the orthopedic device holder 11 and the orthopedic tool 20 can be minimized. For example, since the shaft connection end 14 and the tool connection end 22 are aligned prior to the sleeve 16 encircling the connection, the sideways movement is minimized.

Figure 3:
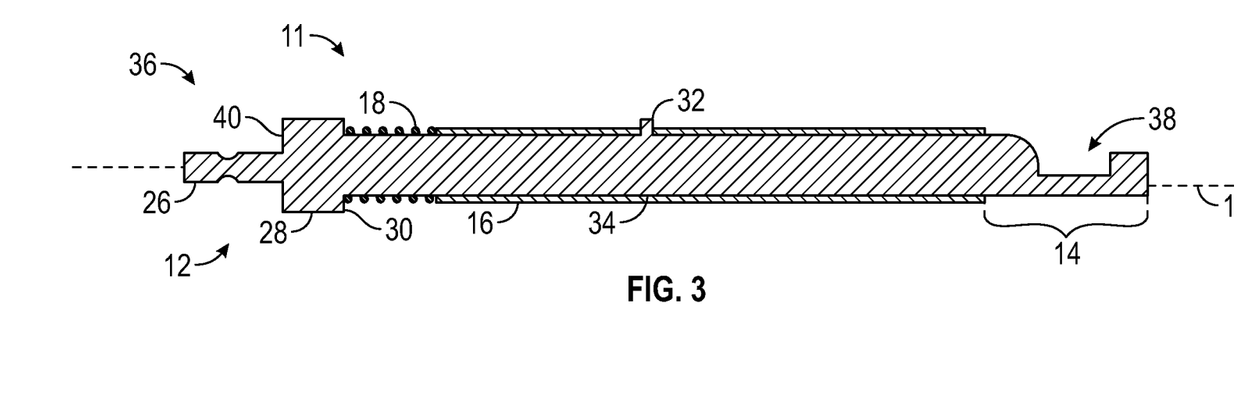
FIG. 3 illustrates a cross-section view of the orthopedic device holder, in accordance with at least one example.

FIG. 3 illustrates a cross-section view of the orthopedic device holder 11, in accordance with at least one example.

The device holder 11 can include a shaft 12, resilient member 18, and sleeve 16. The shaft 12 can include a proximal end 36 and a distal end 38. In an example, the shaft 12 can include a collar portion 28 and an elongate portion 34 extending from the collar portion 28. The elongate portion 34 can extend from the collar portion 28 and terminate at the shaft connection end 14. As shown in FIG. 3, the collar portion 28 can define a first shoulder 30 and a second shoulder 40. The elongate portion 34 can receive the resilient member 18 and the sleeve 16 such that the resilient member 18 abuts (e.g., contacts) the first shoulder 30 of the collar 28 and the sleeve 16 abuts (e.g., contacts) the resilient member 18.

In an example, the proximal end 36 of the shaft 12 can include an engagement end 26. The engagement end 26 can be configured to engage with a turning device. For example, the engagement end 26 can engage with a manual turning device (e.g., a handle), a powered turning device (e.g., drill), or another device such as a slap hammer.

As shown in FIG. 3, the sleeve 16 is in a first position such that the resilient member 18 is in a compressed state and the shaft connection end 14 extends from the sleeve 16. As discussed herein, once the shaft connection end 14 couples with the tool connection end 20, the sleeve 16 can transition to a second position such that the resilient member 18 is in an uncompressed state or a less-compressed state as compared to the compressed state and extends beyond the shaft connection end 14 and encompasses the shaft connection end 14 coupled to the tool connection end 20.

Figure 6:
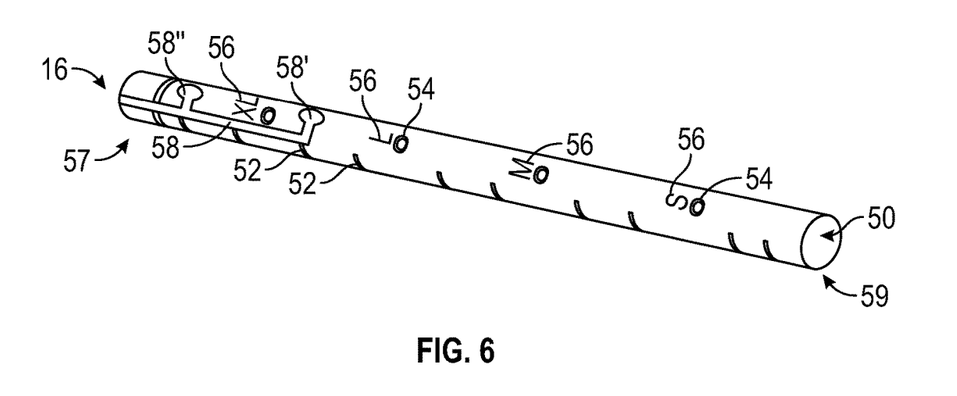
FIG. 6 illustrates a perspective view of a sleeve of the orthopedic device holder, in accordance with at least one example.

In an example, the shaft 12 can include at least one locking projection 32 that extends substantially perpendicular to the longitudinal axis 13 of the shaft 12. The locking projection 32 can engage with a locking slot 58 (as shown in FIG. 6) on the sleeve 16 such that when the sleeve 16 is at the first position or the second position, the sleeve 16 is in a locked configuration with respect to the shaft 12.

Figure 4:
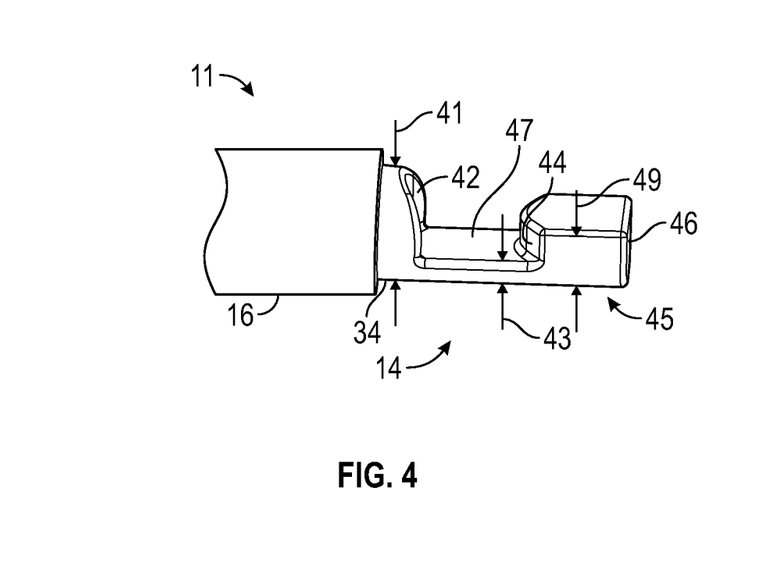
FIG. 4 illustrates a side view of a portion of the orthopedic device holder, in accordance with at least one example.
Figure 7:
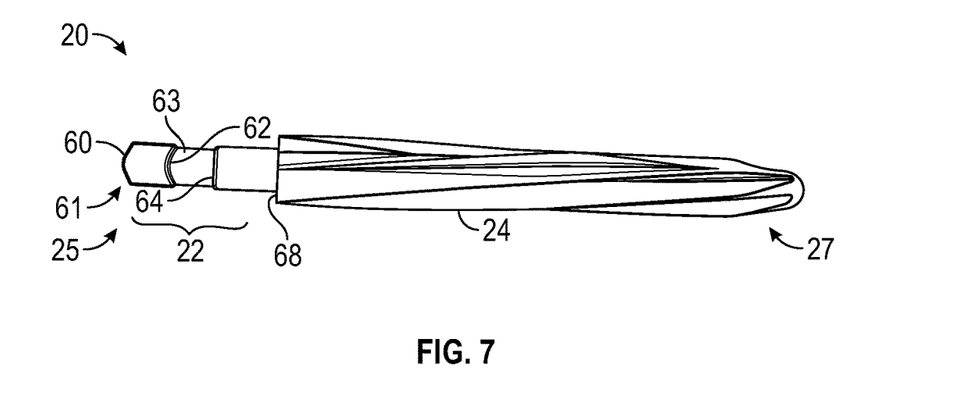
FIG. 7 illustrates a top down view of an orthopedic tool, in accordance with at least one example.

FIG. 4 illustrates a side view of a portion of the orthopedic device holder 11, in accordance with at least one example. Specifically, FIG. 4 illustrates a portion of the device holder 11 including the sleeve 16 and the shaft connection end 14. In an example, the shaft connection end 14 can include three shaft engaging surfaces. For example, the shaft connection end 14 can include a first shaft engaging surface 42, a second shaft engaging surface 44, and a third shaft engaging surface 46. As shown in FIG. 4, the first and second shaft engaging surfaces 42, 44 can include curved surfaces, and the third shaft engaging surface 46 can be a flat surface. The shaft connection end 14 can include a shaft head portion 45 that is bound by the second and third shaft engaging surfaces 44, 46. A shaft flat portion 47 can extend from the first shaft engaging surface 42 to the second shaft engaging surface 44. As discussed herein, the first shaft engaging surface 42, the shaft flat portion 47, and the second shaft engaging surface 44 can define a space configured to receive a tool head portion 61 (as shown in FIG. 7) of the tool connection end 22 of the tool 20.

The shaft flat portion 47 and the shaft head portion 45 can have a reduced thickness (e.g., thickness 43 and thickness 49, respectively) as compared to the thickness 41 of the elongate portion 34 of the shaft 12. As discussed herein, once the shaft connection end 14 engages with the tool connection end 22, the overall thickness can equal the thickness 41 of the elongate portion 34.

Figure 5:
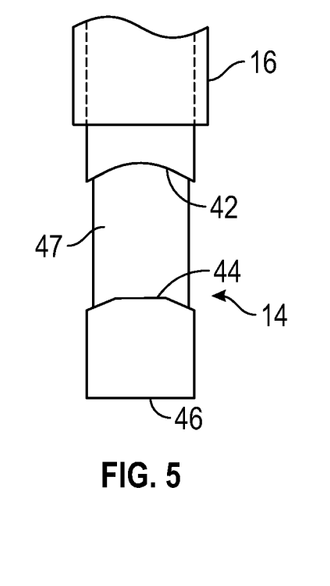
FIG. 5 illustrates a top down view of a portion of the orthopedic device holder, in accordance with at least one example.

FIG. 5 illustrates a top down view of a portion of the orthopedic device holder 11, in accordance with at least one example. As shown in FIG. 5, the first shaft engaging surface 42 and the second shaft engaging surface 44 can have curved surfaces. For example, the first shaft engaging surface 42 can be a concave surface and the second shaft engaging surface 44 can be a convex surface 44. Further, as shown in FIG. 5, the third engaging surface 46 can be a substantially flat surface. While shown as having two curved surfaces and one flat surface, the three engaging surfaces of the shaft connection end 14 can include other shapes and configurations. For example, the first, second, and third shaft engaging surfaces 42, 44, and 46 can be the same or different from each other. However, as discussed herein, the first shaft engaging surface 42 and the first tool engaging surface 60 (as shown in FIG. 7) can be mating opposites of each other and the second shaft engaging surface 44 and the second tool engaging surface 62 (as shown in FIG. 7) can be mating opposites. In one example, the third shaft engaging surface 46 and the third tool engaging surface 64 can each be flat surfaces as shown in FIGS. 5 and 7, or, in an alternative example, surfaces 46 and 64 can include a non-flat surface and be mating opposites of each other.

Figure 13:
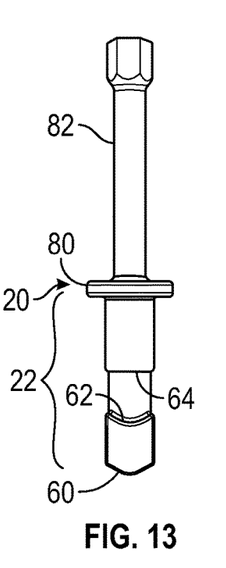
Figure 14:
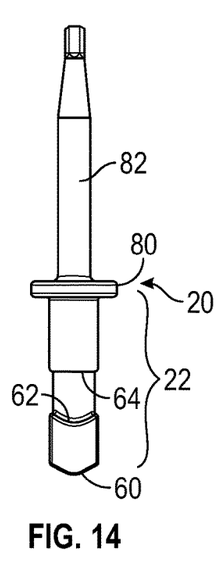

FIG. 6 illustrates a perspective view of the sleeve 16 of the orthopedic tool holder 11, in accordance with at least one example. The sleeve 16 can define a bore 50 and extend from a proximal end 57 to a distal end 59. As discussed herein, the bore 50 can receive the elongate portion 34 of the shaft 12 (shown in FIG. 3). When the sleeve 16 is positioned around the elongate portion 34, the proximal end 57 can abut the resilient member 18 (shown in FIG. 3) and the distal end 59 can abut a portion of the tool 20 (as shown in FIGS. 13 and 14). As shown in FIG. 6, the sleeve 16 can include at least one locking slot 56. Each of the at least one locking slots 58 can be configured to receive at least one locking projection 32 of the shaft 12. The locking slot 58 can include portions 58' and 58". The locking slot portion 58' can be used to hold the sleeve 16 at the first position, where the shaft connection end 14 extends from the sleeve 14. Further, the locking slot portion 58" can be used to hold the sleeve 16 at the second position, where the sleeve 16 extends beyond the shaft connecting end 14 and encircles both the shaft connecting end 14 and the tool connecting end 20 when the device holder 11 is coupled to the tool 20.

In another example, instead of providing at least one locking slot 58, the sleeve 16 can include a groove on the interior surface of the sleeve 16. In that example, the groove can receive the locking projection 32 of the shaft 12 and allow the sleeve 16 to be maintained at either the first or second position. As shown in FIG. 6, the sleeve 16 can include apertures 54 and markings 52 and 56. The apertures 54 can be used to visually aid the surgeon such that they can see the elongated portion 34 of the shaft 12 advance through the sleeve 16. The markings 56 can include letters such as "S", "M", "L", and "XL." As shown in FIG. 6, each marking 56 can be associated with a corresponding aperture 54 and can visually assist the user during a procedure.

Figure 8:
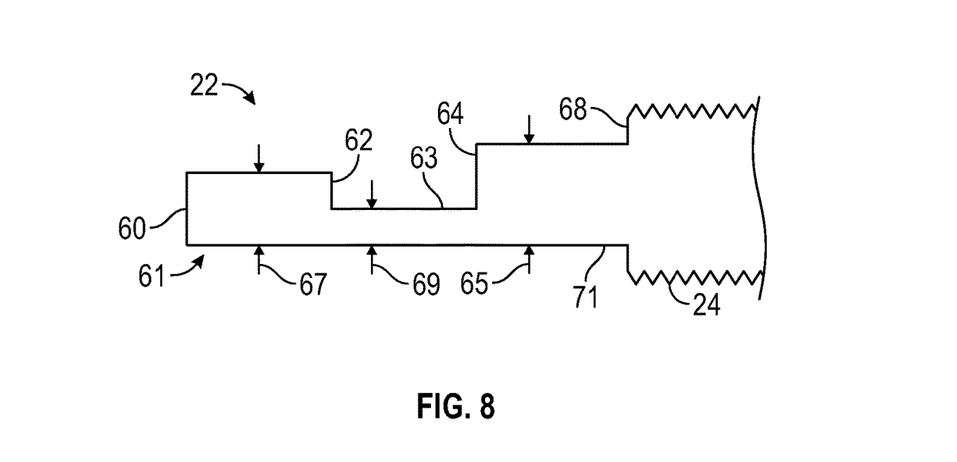
FIG. 8 illustrates a side view of a portion of the orthopedic tool, in accordance with at least one example.

FIG. 7 illustrates a top down view of the orthopedic tool 20, in accordance with at least one example, and FIG. 8 illustrates a side view of a portion of the orthopedic tool 20, in accordance with at least one example. The tool 20 can include the tool connection end 22 located at the proximal end 25 and the orthopedic tool portion 24 (referred to herein as "tool portion 24") located at the distal end 27. The tool portion 24 can define a shoulder 68 that can abut the distal end 59 of the sleeve 16 when the device holder 11 is connected to the tool 20.

As shown in FIGS. 7 and 8, the tool connection end 22 can include three engaging surfaces. For example, the tool connection end 22 can include a first tool engaging surface 60, a second tool engaging surface 62, and a third tool engaging surface 64. As shown in FIG. 7, the first and second tool engaging surfaces 60, 62 can include curved surfaces and the third tool engaging surface 64 can include a flat surface.

The tool connection end 22 can include a tool head portion 61 that is bound by the first and second tool engaging surfaces 60, 62. A tool flat portion 63 can extend from the second tool engaging surface 62 to the third tool engaging surface 64. As discussed herein, the second tool engaging surface 62, the tool flat portion 63, and the third tool engaging surface 64 can define a space configured to receive the shaft head portion 45 (as shown in FIG. 4) of the shaft connection end 14. The tool flat portion 63 and the tool head portion 61 can have a reduced thickness (e.g., thickness 69 and thickness 67, respectively) as compared to the thickness 65 of a shaft portion 71 of the tool connection end 22. As discussed herein, once the tool connection end 22 engages with the shaft connection end 14, the overall thickness can approximately equal the thickness 65 of the shaft portion 71. Further, the thickness 65 can approximately equal the thickness 41 of the elongate portion 34 such that there is a substantially constant thickness from the elongate portion 34, through the connection between the shaft connection end 14 and the tool connection end 22, and to the shaft portion 71 of the orthopedic tool 20.

As shown in FIG. 7, the first tool engaging surface 60 and the second tool engaging surface 62 can have curved surfaces. For example, the first tool engaging surface 60 can be a convex surface and the second tool engaging surface 62 can be a concave surface. As shown in FIG. 7, the third tool engaging surface 64 can be a substantially flat surface. While shown as having two curved surfaces and one flat surface, the three engaging surfaces of the tool connection end 22 can include various other shapes and configurations. For example, the first, second, and third tool engaging surfaces 60, 62, and 64 can be the same or different from each other. However, as discussed herein, the first shaft engaging surface 42 (as shown in FIG. 5) and the first tool engaging surface 60 are mating opposites of each other and the second shaft engaging surface 44 (as shown in FIG. 5) and the second tool engaging surface 62 are mating opposites. In an example, the first shaft engaging surface 42 can be a concave surface and the first tool engaging surface 60 can be a convex surface, and the second shaft engaging surface 44 can be a convex surface and the second tool engaging surface 62 can be a concave surface. The corresponding concave and convex surfaces can also be reversed such that, for example, the first shaft engaging surface 42 is convex and the first tool engaging surface 60 is concave. In an example, the third shaft engaging surface 46 and the third tool engaging surface 64 can each be flat surfaces, as shown in FIGS. 5 and 7, or surfaces 46 and 64 can be mating opposites, as shown in FIG. 10.

As discussed herein, the three shaft engaging surfaces 42, 44, and 46 and the three tool engaging surfaces 60, 62, and 64 can have various configurations. However, the first shaft engaging surface 42 and the first tool engaging surface 60 are mating opposites and the second shaft engaging surface 44 and the second tool engaging surface 62 are mating opposites. As will be appreciate by one or ordinary skill in the art, providing the first and second shaft and tool engaging surfaces 42, 44, 60, and 62 with non-flat surfaces can prevent rotation of the device holder 11 and the tool 20 when coupled together. In one example, the third shaft and tool engaging surfaces 46 and 64 can include flat surfaces as discussed above. In another example, the third shaft and tool engaging surfaces 46 and 64 can include non-flat surfaces.

Figure 9:
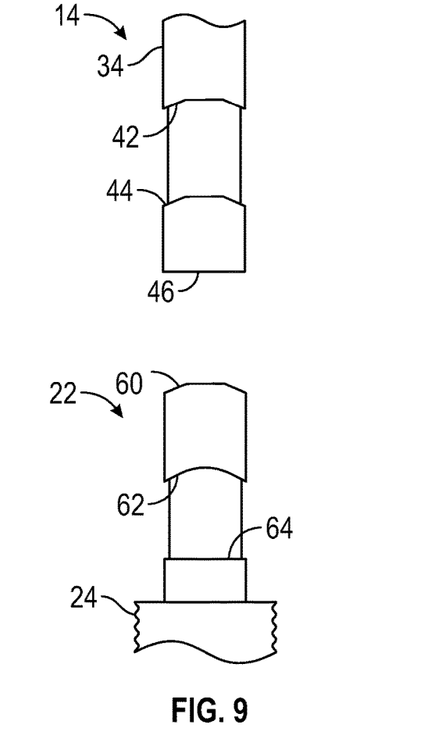
FIG. 9 illustrates a top down view of a shaft connection end and a tool connection end, in accordance with at least one example.
Figure 10:
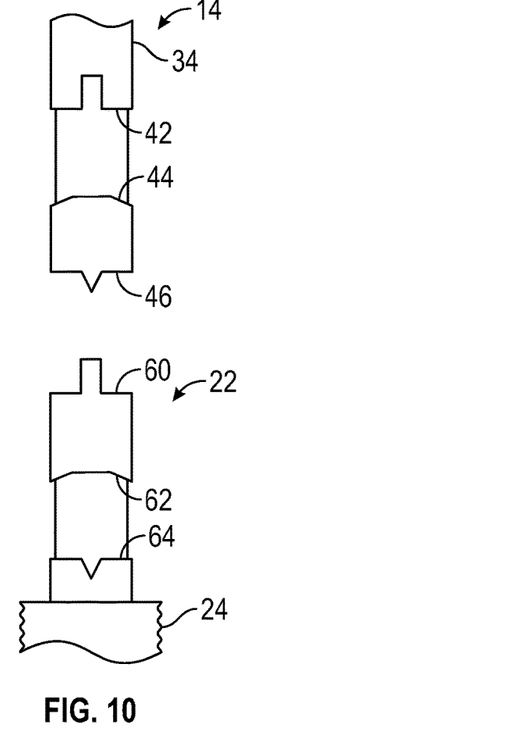
FIG. 10 illustrates a top down view of a shaft connection end and a tool connection end, in accordance with at least one example.

FIGS. 9 and 10 illustrate top down views of shaft connection ends 14', 14" and tool connection ends 22', 22" in accordance with various examples. Specifically, FIGS. 9 and 10 illustrate various configurations of three shaft engaging surfaces and the three tool engaging surfaces. As shown in FIG. 9, the first and second shaft and tool engaging surfaces 42', 44', and 60', 62' each include a flat surface and two curved surfaces, while the third shaft and tool engaging surfaces 46' and 64' include flat surfaces.

As shown in FIG. 9, the first shaft engaging surface 42' and the first tool engaging surface 60' include mating opposites. That is, the first shaft engaging surface 42' includes a flat surface and two concave curved surfaces and the first tool engaging surface 60' includes a flat surface and two convex curved surfaces. Similarly, the second shaft engaging surface 44' and the second tool engaging surface 63' include mating opposites. For example, the second shaft engaging surface 44' includes a flat surface and two convex curved surfaces and the second tool engaging surface 62' includes a flat surface and two convex curved surfaces.

FIG. 10 illustrates another example of the three shaft and tool engaging surfaces. In the example illustrated in FIG. 10, the first shaft and tool engaging surfaces 42", 60" can be non-curved surfaces. The first shaft engaging surface 42" can include a flat surface with a recess defined therein. The first tool engaging surface 60" can include a flat surface with a projection extending therefrom, wherein the projection is configured to be received within the recess of the first shaft engaging surface 42". As shown in FIG. 10, the second shaft engaging surface 44" and the second tool engaging surface 62" can each include a flat surface and two curved surfaces. Further, the third shaft engaging surface 46" can define a projection and the third tool engaging surface 69" can define a recess configured to receive the projection. Thus, regardless of the shapes defined by the three shaft and tool engaging surfaces, at least the first shaft and tool engaging surfaces are mating opposites and the second shaft and tool engaging surfaces are mating opposites. As discussed herein, the third shaft and tool engaging surfaces can include flat surfaces or matting opposites.

Figure 11A:
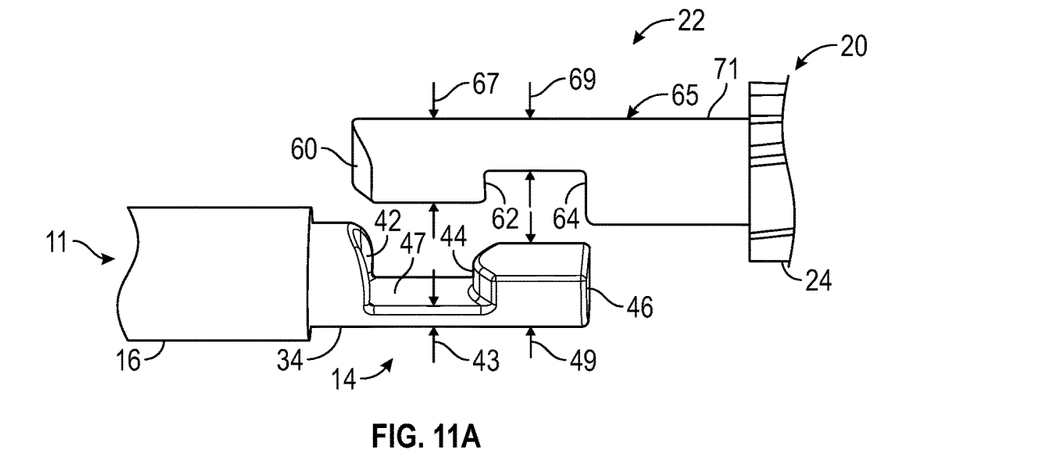
FIGS. 11A-11C illustrate stages of connecting the orthopedic device holder with the orthopedic tool, in accordance with at least one example.
Figure 11B:
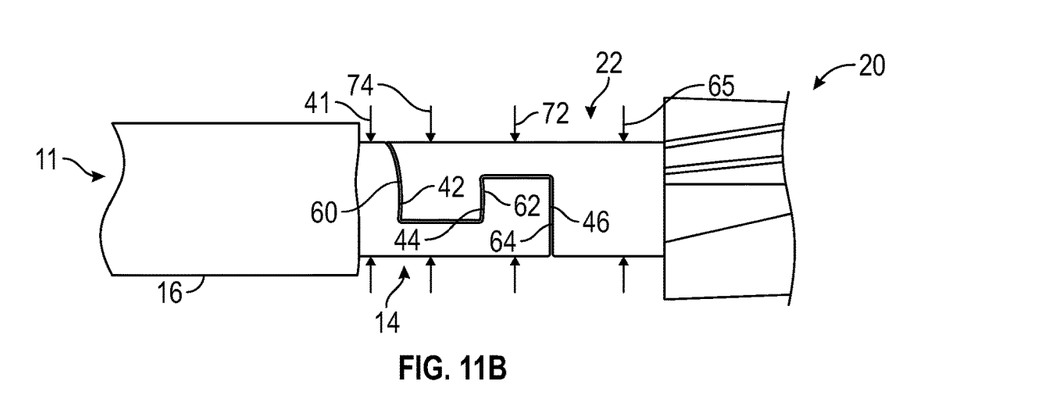
Figure 11C:
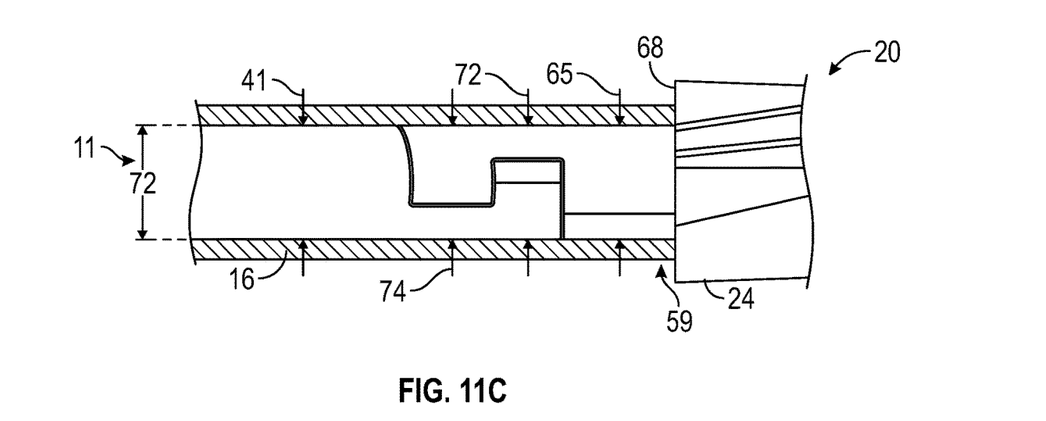

FIGS. 11A-11C illustrate stages of connecting the orthopedic tool holder 11 with the orthopedic tool 20, in accordance with at least one example. As shown in FIG. 11A, the sleeve 16 is in the first position. That is, the resilient member 18 is in a compressed state and the shaft connection end 14 extends from the sleeve 16. In the first sleeve position, the tool connection end 22 can couple with the shaft connection end 14 such that the first shaft engaging surface 42 mates with the first tool engaging surface 60, the second shaft engaging surface 44 mates with the second tool engaging surface 62, and the third shaft engaging surface 46 mates with the third tool engaging surface 64.

FIG. 11B illustrates the shaft connection end 14 and the tool connection end 22 coupled together. As shown in FIG. 11B, a total thickness 72 of the thicknesses 67 and 49 (see FIG. 11A) is substantially equal to the thickness 65 of the tool shaft portion 71 and the thickness 41 of the elongate portion 34 of the shaft 12. Additionally, a total thickness 74 of the thicknesses 67 and 43 (see FIG. 11A) is substantially equal to the thickness 65 of the tool shaft portion 71 and the thickness 41 of the elongate portion 34 of the shaft 12.

As discussed herein, once the shaft connection end 14 and the tool connection end 22 are coupled together, the sleeve 16 can transition from the first position to the second position. At the second position, the resilient member 18 is in an uncompressed or less-compressed state as compared to the compressed state and the sleeve 16 extends to at least the end of the shaft connection end 14. In an example, at the second position, the sleeve 16 extends beyond the shaft connection end 14 and encircles the shaft connection end 14 and the tool connection end 22. As shown in FIG. 11C, the sleeve 16 can advance until the distal end 59 of the sleeve 16 contacts a shoulder 68 defined by the tool portion 24. In another example, the tool portion 20 can include a collar portion 80 (as shown in FIGS. 12-15) and the sleeve 16 can contact the collar portion 80 when in the second position.

As illustrated in FIG. 11C, the thicknesses 41, 74, 72, and 65 are substantially equal to each other and are substantially similar to the diameter 72 of the bore 50 defined by the sleeve 16. The difference between the thicknesses 41, 74, 72, and 65 and the diameter 72 of the bore 50 should be great enough to allow the sleeve 16 to be moveable about the shaft 12, but small enough such that movement between the shaft connection end 14 and the tool connection end 20 is minimized.

Figure 12:
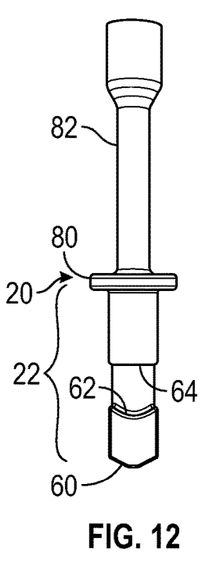
FIGS. 12-15 illustrate various orthopedic tools that can be used with the orthopedic device holder, as constructed in accordance with at least one example.
Figure 15:
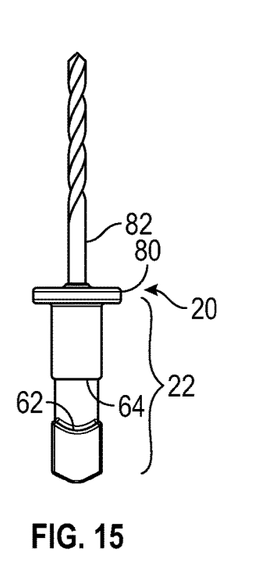

FIGS. 12-15 illustrate various orthopedic tools 20 that can be used with the orthopedic device holder 11, as constructed in accordance with at least one example. As illustrated in FIGS. 12-15, the orthopedic tools 20 can include a tool connection end 22, a collar 80, and a tool portion 82. As shown in FIGS. 12-15, the tool portion 82 can include, but is not limited to, a socket driver (as shown in FIG. 12), a large hex driver (as shown in FIG. 13), a small hex driver (as shown in FIG. 14), and a drill bit (as shown in FIG. 15).

It is recognized that there are other designs of orthopedic tools, which can incorporate the tool connection end to couple with the orthopedic tool holder. For example, other types of tools can include reaming, extraction, impaction, and investigation devices (e.g, cameras, lights, probes, and sensors).

A method of making the orthopedic device holder system can include forming an orthopedic device holder having a shaft including a collar, an elongated portion extending from the collar, and a shaft connection end. The shaft connection end can include a first shaft engaging surface, a second shaft engaging surface, and a third shaft engaging surface. The method can include forming an orthopedic tool having a tool connection end configured to engage with the shaft connection end and a tool portion. The tool connection end can include a first tool engaging surface, a second tool engaging surface, and a third tool engaging surface. In an example, the first shaft engaging surface and the first tool engaging surface have opposite mating surfaces, and the second shaft engaging surface and the second tool engaging surface have opposite mating surfaces. The method can include positioning a resilient member around the shaft, and positioning a sleeve around the shaft and adjacent to the resilient member.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An orthopedic device holder system, comprising:
   an orthopedic device holder, including:
      a shaft having a proximal end and a distal end, the shaft including a shaft connection end positioned at the distal end of the shaft, the shaft connection end having at least three shaft engaging surfaces; and
   an orthopedic tool having a proximal end and a distal end, the orthopedic tool configured to be coupled to the orthopedic device holder, the orthopedic tool, including:
      a tool connection end positioned at the proximal end of the orthopedic tool configured to engage with the shaft connection end, the tool connection end having at least three tool engaging surfaces; and
      an orthopedic tool portion,
   wherein a first shaft engaging surface is configured to mate with a first tool engaging surface, a second shaft engaging surface is configured to mate with a second tool engaging surface, and a third shaft engaging surface is configured to mate with a third tool engaging surface, wherein the first shaft engaging surface and the second tool engaging surface have a concave shape and the second shaft engaging surface and the first tool engaging surface have a convex shape.

2. The orthopedic device holder system of claim 1, wherein the first shaft engaging surface and the first tool engaging surface have opposite mating surfaces, the second shaft engaging surface and the second tool engaging surface have opposite mating surfaces, and the third shaft engaging surface and the third tool engaging surface have a similar mating surface.

3. The orthopedic device holder system of claim 1, wherein the first and second shaft engaging surfaces and the first and second tool engaging surfaces have non-flat surfaces and the third shaft engaging surface and the third tool engaging surface have a flat surface.

4. The orthopedic device holder system of claim 1, wherein the shaft includes a collar portion and an elongate portion extending from the collar portion.

5. The orthopedic device holder system of claim 4, wherein the elongate portion extends between the collar portion and the shaft connection end.

6. The orthopedic device holder system of claim 4, further including:
   a resilient member positioned around the elongate portion adjacent to the collar portion; and
   a sleeve positioned around the shaft and adjacent to the resilient member.

7. The orthopedic device holder system of claim 6, wherein the sleeve defines a bore that receives the elongate portion of the shaft.

8. The orthopedic device holder system of claim 6, wherein the sleeve is moveable between a first position and a second position, such that in the first position the resilient member is in a compressed state and the shaft connection end extends from the sleeve and in the second position, the resilient member is in an less compressed state as compared to the compressed state such that the shaft connection end and the tool engaging end are positioned within the sleeve.

9. The orthopedic device holder system of claim 8, wherein, at the second position, a distal end of the sleeve abuts the orthopedic tool portion.

10. The orthopedic device holder system of claim 6, wherein the elongate portion includes a locking projection.

11. The orthopedic device holder system of claim 10, wherein the sleeve defines a locking slot that is configured to receive the locking projection, the sleeve moveable between an unlocked position and a locked position, such that in the unlocked position, the sleeve is movable relative to the elongate portion and in the locked position, the sleeve is fixed relative to the elongate portion.

12. The orthopedic device holder of claim 1, wherein the proximal end of the shaft includes an engagement end configured to receive a turning device.

13. The orthopedic device holder of claim 1, wherein the shaft defines a longitudinal axis and the three shaft engaging surfaces are perpendicular to the longitudinal axis.

14. An orthopedic device holder system, comprising:
   an orthopedic device holder, including:
      a shaft having a shaft connection end having at least a first shaft engaging surface, a second shaft engaging surface, and a third shaft engaging surface;
      a resilient member positioned around the shaft; and
      a sleeve positioned around the shaft and adjacent to the resilient member; and
   an orthopedic tool having a tool connection end configured to engage with the shaft connection end, the tool connection end having a first tool engaging surface, a second tool engaging surface, and a third tool engaging surface, wherein the first shaft engaging surface is configured to mate with the first tool engaging surface, the second shaft engaging surface is configured to mate with the second tool engaging surface, and the third shaft engaging surface is configured to mate with the third tool engaging surface, and wherein the sleeve is configured to move between a first position and a second position such that at the first position, the shaft connection end extends from the sleeve and at the second position, the shaft connection end and the tool connection end are positionable within the sleeve.

15. The orthopedic device holder system of claim 14, wherein the first shaft engaging surface and the first tool engaging surface have opposite mating surfaces, and wherein the second shaft engaging surface and the second tool engaging surface have opposite mating surfaces.

16. The orthopedic device holder system of claim 14, wherein the third shaft engaging surface and the third tool engaging surface have flat surfaces.

17. The orthopedic device holder system of claim 14, wherein the third shaft engaging surface and the third tool engaging surface have opposite mating surfaces.

18. A method of making an orthopedic device holder system; comprising:

forming an orthopedic device holder having a shaft including a collar; an elongated portion extending from the collar, and a shaft connection end, the shaft connection end including at least a first shaft engaging surface, a second shaft engaging surface, and a third shaft engaging surface; and forming an orthopedic tool having a tool connection end configured to engage with the shaft connection end and a tool portion; the tool connection end having at least a first tool engaging surface, a second tool engaging surface, and a third tool engaging surface, wherein the first shaft engaging surface and the first tool engaging surface have opposite mating surfaces; and the second shaft engaging surface and the second tool engaging surface have opposite mating surfaces, wherein the first shaft engaging surface and the second tool engaging surface have a concave shape and the second shaft engaging surface and the first tool engaging surface have a convex shape.

19. The method of claim 18, wherein forming the orthopedic device holder further includes:

positioning a resilient member around the shaft; and positioning a sleeve around the shaft and adjacent to the resilient member.

\* \* \* \* \*